United States Patent [19]

Hara et al.

[11] 4,271,253

[45] Jun. 2, 1981

[54] METHOD FOR STABILIZING ORGANIC SUBSTRATE MATERIALS INCLUDING PHOTOGRAPHIC DYE IMAGES TO LIGHT AND PHOTOGRAPHIC MATERIAL SO STABILIZED

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 150,028

[22] Filed: May 15, 1980

Related U.S. Application Data

[62] Division of Ser. No. 969,518, Dec. 14, 1978.

[30] Foreign Application Priority Data

Dec. 14, 1977 [JP] Japan ................. 52-150344

[51] Int. Cl.$^3$ .................... G03C 1/10; G03C 1/40; G03C 1/84

[52] U.S. Cl. .................... 430/216; 430/17; 430/211; 430/372; 430/512; 430/551; 430/559; 430/517; 430/518

[58] Field of Search ............... 430/17, 211, 216, 512, 430/517, 518, 372, 557, 559; 260/45.75 N, 45.75 R; 8/74

[56] References Cited

U.S. PATENT DOCUMENTS 4,050,938  9/1977  Smith et al. .................... 430/170

*Primary Examiner*—Richard L. Schilling
*Attorney, Agent, or Firm*—Sughrue, Rothwell, Mion, Zinn and Macpeak

[57] ABSTRACT

A method of stabilizing an organic substrate material such as a photographic dye against the action of light having an absorption maximum between about 300 nm and about 800 nm in wavelength by making co-exist with the organic substrate material at least one compound represented by the formula (I) defined in the specification is disclosed.

2 Claims, No Drawings

METHOD FOR STABILIZING ORGANIC SUBSTRATE MATERIALS INCLUDING PHOTOGRAPHIC DYE IMAGES TO LIGHT AND PHOTOGRAPHIC MATERIAL SO STABILIZED

This is a Division of application Ser. No. 969,518, filed Dec. 14, 1978.

BACKGROUND OF THE INVENTION

1. Field of the Invention

This invention relates to a method for stabilizing organic substrate materials to light, and more particularly to a method for stabilizing organic compounds, especially organic dyes and photographic dye images to light.

2. Brief Description of the Prior Art

In general, it is accepted that organic substances, for example, such as organic dyes tend to fade by the action of light. Extensive investigations have been carried out in various technical fields including those for printing ink, textile dyeing as well as color photography, attempting to enhance light fastness of organic dyes.

The present invention is advantageously applied to the improvement of the light fastness of these organic substrate materials.

In the following description, the term "organic substrate material" or "organic substrate" refers to materials appearing colored or colorless to human vision under the illumination of sunlight, including not only those with the absorption maximum in the visible region of spectrum, but also those the absorption maximum of which lies in the ultraviolet region as in the case of optical whitening agent or in the infrared. Phrased differently, the organic substrate materials of the present invention include those having their absorption maxima at the wavelength of from 300 to 800 nm. These organic substrate materials occur particularly in photographic materials, e.g., color films, prints, diffusion transfer units, etc., in colored polymers useful as agricultural vinyl cover sheets, umbrellas, tents, etc.; fluorescent whitening agents; and dyed textiles, etc., and this invention is directed to improving the light fastness of these materials in each of these environments.

In the present specification, the term "dye" or "dyestuff" refers to organic materials which appear colored to the human eye under the illumination of sunlight.

In the present specification, the term "light" conceptually involves electromagnetic radiation with wavelengths up to about 800 nm, thus including ultraviolet ray below 400 nm, visible light of from about 400 nm to about 700 nm and infrared or from about 700 nm to about 800 nm.

It is already widely known that organic substrate materials such as dyes or dyestuffs tend to fade under the influence of light irradiation; and a number of technical reports dealing with the methods of suppressing such a tendency or of improvement of the light fastness of such materials are known. For example, U.S. Pat. No. 3,432,300 discloses that the light fastness of organic compounds such as indophenol, indaniline, azo and azomethine dyes against visible and UV light is improved by the use of certain phenol derivatives containing a fused heterocyclic structure. As is described in, C. E. K. Mees and T. H. James, *The Theory of the Photographic Process*, Chapter 17, published by Macmillan Inc., (1967), silver halide color photographic products generally give rise to azomethine or indaniline dyes formed by the reaction of the oxidation product from an aromatic primary amine developing agent with a coupler. A number of techniques are known with respect to methods for improving the stability of images obtained from these dyes, that is, colored images, to light; for example, there are known hydroquinone derivatives as described in U.S. Pat. Nos. 2,360,290, 2,418,613, 2,675,314, 2,701,197, 2,704,713, 2,728,659, 2,732,300, 2,735,765, 2,710,801, and 2,816,028, British Pat. No. 1,363,921, etc.; gallic acid derivatives as described in U.S. Pat. Nos. 3,457,079 and 3,069,262, Japanese Patent Publication 13496/1968, etc.; p-alkoxyphenol derivatives as described in U.S. Pat. Nos. 2,735,765 and 3,698,909; chroman or coumarane derivatives as described in U.S. Pat. Nos. 3,432,300, 3,573,050, 3,574,627, 3,764,337, 3,574,626, 3,698,909 and 4,015,990 and the like. These compounds are effective to prevent the fading or discoloration of dye images induced by light to a certain extent, but not to a satisfactory extent.

British Pat. No. 1,451,000 discloses that the stability to light of organic substrate materials is enhanced by the use of azomethine quenching compounds which have their absorption-maximum at a longer wavelength than the substrate material; however, unfortunately the fact that the azomethine quenching compound is colored itself adversely affects the color hue of the substrate material.

Further, metal chelates can be used for the prevention of degradation of polymeric substances caused by the action of light as is described in J. P. Guillory and R. S. Becker, *J. Polym. Sci. Ed.*, 12, 993 (1974), and R. P. R. Ranaweera & G. Scott, *J. Polym. Sci.*, Polym. Let. Ed., 13, 71(1975), etc. Stabilization of dyes against light by the use of metal chelates is also described in Japanese Patent Application (OPI) 87649/1975 and *Research Disclosure*, 15162(1976). However, the disclosed metal chelates exhibit an unsatisfactory light fastness together with an undesirably poor solubility in common organic solvents. The latter imposes a limitation on the working concentration of such a chelates in the system in concern, thus leading to an insufficient function of light fastness. Moreover, these chelates cannot be present in a high concentration since they themselves are comparatively deeply colored, adversely affecting the color hue and color purity of the dyes to be protected.

In addition to the foregoing, agents suitable for improving the light fastness of cyan dyes and particularly cyan dye images have not been known.

SUMMARY OF THE INVENTION

Accordingly, a principal object of the present invention is to provide a method for stabilizing organic substrate materials to light.

Another object of the present invention is to provide a method for improving the stability of these materials to light without deteriorating the color hue and as well as color purity of organic substrate materials such as, in particular, dyes or coloring agents.

Still another object of the present invention is to provide a method for enhancing the stability of organic substrate materials against light by the use of stabilizing agents which are readily soluble in organic solvents and which are highly compatible with various organic substrate materials.

Another object of the present invention is to provide a method for improving the stability against light of dye images composing color photographs.

Another object of the present invention is to provide a method for improving the stability to light of dyestuffs resulting from the reaction of an aromatic primary amine developing agent with a color coupler.

Still another object of this invention is to improve the light fastness of colored polymers such as are used in agricultural vinyl sheets, umbrellas, tents, etc.

These objects and other objects of the present invention will become more apparent from the following description of the specification.

DETAILED DESCRIPTION OF THE INVENTION

The above described objects of the present invention have been achieved by making co-exist a compound represented by the following formula (I) with an organic substrate material having an absorption maximum between about 300 and about 800 nm in wavelength.

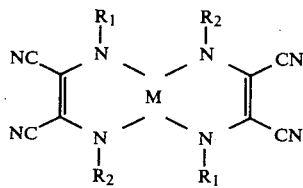

wherein M represents Ni, Pd or Pt; $R_1$ and $R_2$ each represents a hydrogen atom, an alkyl group, an aryl group, an acyl group, an alkoxycarbonyl group, an aryloxycarbonyl group, an alkylsulfonyl group, an arylsulfonyl group, or a carbamoyl group which may be the same or different.

The terms "in the presence of" or "coexistant with" as used in the specification refer not only to co-existence of the substrate material and the compound of the formula (I) in the same solution, dispersion, emulsion or layer but also to the existence of the organic substrate and the complex in, for example, adjacent layers of a multi-layered photographic material. As long as the complex compound is associated with the organic substrate material such that it improves the light fastness of the organic substrate, it is used "in the presence of" or "coexists" with the substrate for purposes of the present invention.

The alkyl group represented by $R_1$ or $R_2$ includes both substituted and unsubstituted alkyl groups, which may be straight chain or branched chain alkyl groups. These alkyl groups are alkyl groups having preferably 1 to 20 carbon atoms excluding the carbon atoms in any substituent portion, which can be exemplified by a methyl group, an ethyl group, a propyl group, a butyl group, a hexyl group, an octyl group, a decyl group, a dodecyl group, a tetradecyl group, a hexadecyl group, a heptadecyl group or an octadecyl group, etc.

The aryl groups represented by $R_1$ and $R_2$ include both substituted and unsubstituted aryl groups, and preferably those which are monocyclic or bicyclic having 6 to 14 carbon atoms which can be exemplified by a phenyl group, a tolyl group, a naphthyl group, etc.

The acyl groups represented by $R_1$ and $R_2$ include both substituted and unsubstituted acyl groups, preferably having 2 to 21 carbon atoms excluding the carbon atoms in any substituent moiety, which can be exemplified by an acetyl group, a valeryl group, a stearoyl group, a benzoyl group, a naphthoyl group, etc.

The alkoxycarbonyl groups represented by $R_1$ and $R_2$ include both substituted and unsubstituted alkoxycarbonyl groups, preferably having 2 to 21 carbon atoms excluding the carbon atoms in any substituent moiety, which can be exemplified by a methoxycarbonyl grop, a butoxycarbonyl group, a propoxycarbonyl group, etc.

The aryloxycarbonyl groups represented by $R_1$ and $R_2$ include both substituted and unsubstituted aryloxycarbonyl groups, preferably having 7 to 15 carbon atoms excluding the carbon atoms in any substituent moiety, which can be exemplified by a phenoxycarbonyl group, a tolyloxycarbonyl group, etc.

The alkylsulfonyl groups represented by $R_1$ and $R_2$ include both substituted and unsubstituted alkylsulfonyl groups, preferably having 1 to 20 carbon atoms excluding the carbon atoms at the substituent moiety, which can be exemplified by a mesyl group, a butanesulfonyl group, etc.

The arylsulfonyl groups represented by $R_1$ and $R_2$ include both substituted and unsubstituted arylsulfonyl groups, preferably having 6 to 14 carbon atoms excluding the carbon atoms in any substitutent moiety, which can be exemplified by a benzenesulfonyl group, a tosyl group, etc.

The carbamoyl groups represented by $R_1$ and $R_2$ include both substituted and unsubstituted carbamoyl groups, which can be exemplified by an N-phenylcarbamoyl group, an N-p-tolycarbamoyl group, etc.

The alkyl, aryl, acyl, alkoxycarbonyl, aryloxycarbonyl, alkylsulfonyl arylsulfonyl and carbamoyl groups represented by $R_1$ and $R_2$ described above may be substituted with a halogen atom (e.g., a chlorine atom, a bromine atom, or a fluorine atom, etc.), a cyano group, a straight or branched chain substituted or unsubstituted alkyl group (e.g., a methyl group, an ethyl group, a propyl group, a butyl group, a hexyl group, an octyl group, a decyl group, a dodecyl group, a tetradecyl group, a hexadecyl group, a heptadecyl group, an octadecyl group, a methoxyethoxyethyl group, etc.), a substituted or unsubstituted aryl group (e.g., a phenyl group, a tolyl group, a naphthyl group, a chlorophenyl group, a methoxyphenyl group, an acetylphenyl group, etc.), a substituted or unsubstituted alkoxy group (e.g., a methoxy group, an ethoxy group, a butoxy group, a propoxy group, a methoxethoxy group, etc.), a substituted or unsubstituted aryloxy group (e.g., a phenoxy group, a tolyloxy group, a naphthoxy group, a methoxyphenoxy group, etc.), a substituted or unsubstituted aralkyl group (e.g, benzyl group, a phenethyl group, an anisyl group, etc.), a substituted or unsubstituted alkoxycarbonyl group (e.g., a methoxycarbonyl group, a phenoxymethyoxycarbonyl group, a butoxycarbonyl group, etc.), a substituted or unsubstituted aryloxycarbonyl group (e.g., a phenoxycarbonyl group, a tolyloxycarbonyl group, a methoxyphenoxycarbonyl group, etc.), a substituted or unsubstituted acyl group (e.g., a formyl group, an acetyl group, a valeryl group, a stearoyl group, a benzoyl group, a toluoyl group, a naphthoyl group, a p-methoxybenzoyl group, etc.), a substituted or unsubstituted acyloxy group (e.g., an acetoxy group, a benzoyloxy group, a p-methoxybenzoyloxy group, etc.), a substituted or unsubstituted acylamino group (e.g., an acetamido group, a benzamido group, a methoxyacetamido group, etc.), a substituted or unsubstituted anilino group (e.g., a phenylamino group, an N-methylanilino group, an N-phenylanilino group, an N-acetylanilino group, etc.), an alkylamino group, (e.g., an n-butylamino group, an N,N-diethylamino group, a 4-methoxy-n-butylamino group, etc.), a substituted or unsubstituted carbamoyl group (e.g., an n-butylcarbamoyl group, an N-(4-methoxy-n-butyl)carbamoyl group, etc.), a substituted or unsubstituted sulfamoyl group (e.g., an n-butylsulfamoyl group, an N,N-diethylsulfamoyl group, an n-dodecylsulfamoyl group, an N-(4-methoxy-n-butyl)sulfamoyl group, etc.), a substituted or unsubstituted sulfonylamino group (e.g., a methylsulfonylamino group, a phenylsulfonylamino group, a methoxymethylsulfonylamino group, etc.), a substituted or unsubstituted sulfonyl group (e.g., a mesyl group, a tosyl group, a methoxymethanesulfonyl group, etc.), or the like, wherein the above substituents any alkyl moiety is straight or branced and contains 1 to 20 carbon atoms and any aryl moiety is monocyclic or bicyclic, and contains 6 to 14 carbon atoms.

Of the complexes represented by the formula (I), the complexes which are preferably employed in the present invention are those wherein M represents Ni.

Compounds represented by the following structural formulae are complexes which fall within the formula (I) described above and are listed for the purpose of illustrating particularly suited compounds for practicing the present invention, but the present invention is not deemed to be limited thereto.

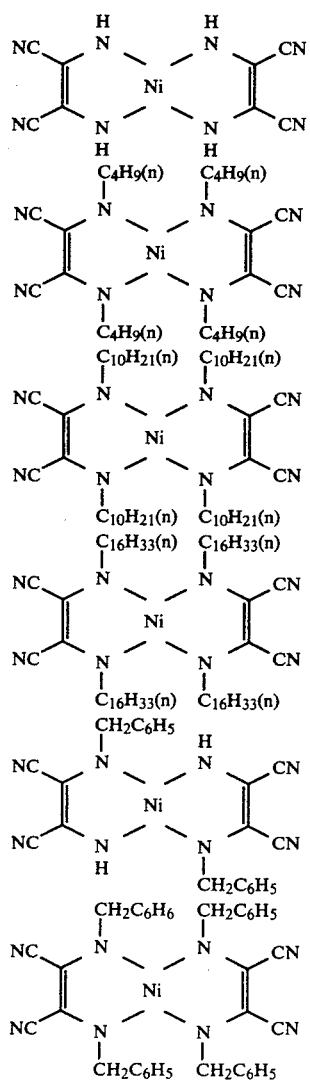

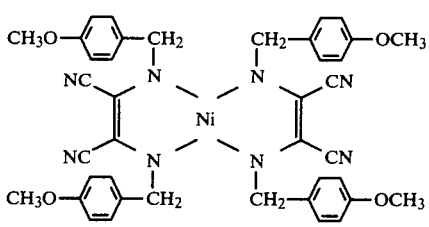

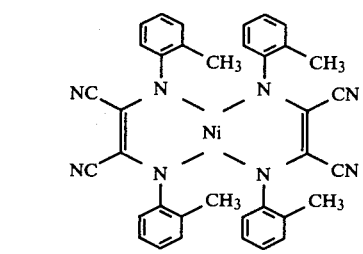

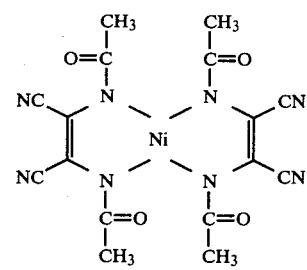

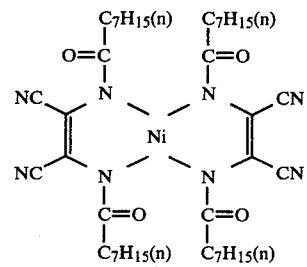

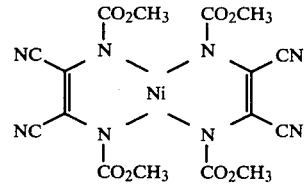

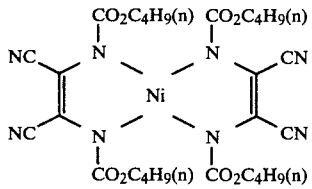

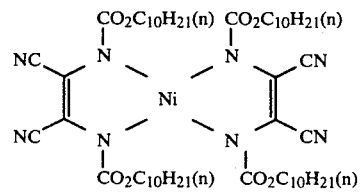

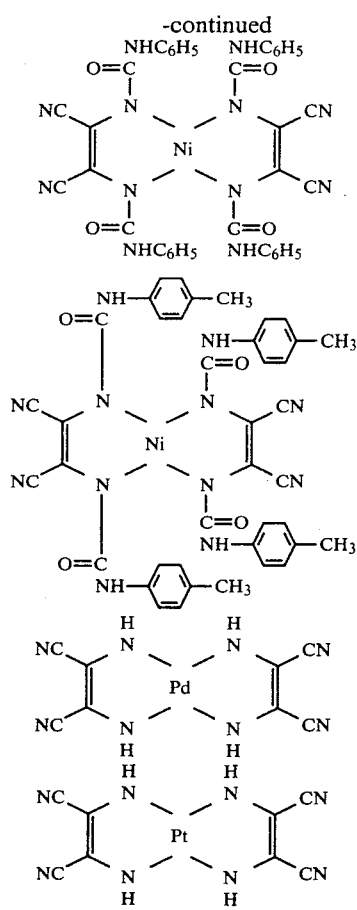

General procedures for synthesizing these chelate compounds are given in, for example, M. G. Miles, M. B. Hursthouse and A. G. Robinson, *J. inorg. nucl. Chem.*, 33, page 2015(1971). A basic ethanolic solution containing diaminomaleonitrile or derivatives thereof and nickel chloride hexahydrate in an equimolar amount is stirred at room temperature for an hour. The crystals of the complex precipitated are separated and, if necessary, recrystallized in a conventional manner.

Synthesis of Compound I-1

A solution of 8.6 g of diaminomaleonitrile in 500 ml. of ethanol was dropwise added to a solution of 9.5 g of nickel chloride hexahydrate in 500 ml. of water at room temperature with stirring. Thereto was dropwise added as a base 100 ml. of a solution of 8.9 g of 2,6-dimethylpiperidine in 100 ml. of ethanol at room temperature while stirring. Stirring was continued for further about 1 hr. The resulting solution was condensed to precipitate crystals. The crystals were filtered and extracted with acetone. The acetone solution was condensed. The so obtained acetone-soluble solid was recrystallized from acetonitrile.

Synthesis of Compound I-5

2.30 g of N,N'-dibenzylaminomaleonitrile which had been synthesized in accordance with an article *The Journal of Organic Chemistry*, 39, 2341(1974) was dissolved in 100 ml. of ethanol. The solution was dropwise added slowly to a solution of 0.95 g. of nickel chloride hexahydrate in 50 ml. of water with stirring at room temperature. Further, a solution of 0.89 g. of triethylamine in 10 ml. of ethanol was added thereto as a base.

Stirring was continued at room temperature for further one hour. The solvent was removed from the resulting solution by evaporation and the residue was extracted with acetone. Acetone was evaporated off from the acetone solution. The so obtained solid was recrystallized from acetonitrile.

As will be apparent from the extensive discussion and examples of the organic substrate which follows. The present invention is effective with a very wide variety of organic materials, the essential point being that the substrate material have a maximum absorption wavelength in the ragne of 300 to 800 nm.

The organic substrate material of the present invention includes all of the dyestuffs belonging to various groups classified from a viewpoint of dyeing property, i.e., water soluble dyes such as basic, acidic, direct, water-soluble vat and mordant dyes, etc., water-insoluble dyes such as sulfur, vat, oil-soluble, dispersion, azoic and oxidative dyes, etc., and reactive dyes. Not only compounds which appear colored under the illumination of sunlight, but also colorless or pale yellow dyes such as fluorescent whitening agents are included in the organic substrate material defined in the present invention.

Of these dyes, dyes which are particularly preferred for the application of the present invention include quinoneimine dyes (e.g., azine, oxazine, thiazine dyes, etc.), methine and polymethine dyes (e.g., cyanine, azomethine and the like), azo dyes, anthraquinone dyes, indamine dyes, indophenol dyes, indigoid dyes, carbonium dyes, formazan dyes, etc., classified depending upon chemical structure.

The organic substrate material associated with the present invention includes dyes composing photographic images including, for example, those resulting from color couplers, DRR compounds, DDR couplers, aminolazone derivatives, dye developers, etc., those used for silver dye bleach process, etc.

More specifically, anthraquinone, quinoneimine, azo methine, polymethine, indamine, indophenol and formazan types of dyes are particularly preferred as the organic substrate material in accordance with the present invention.

The most favorably employed in the practicing the present invention include methine and polymethine dyes as well as indamine and indophenol dyes. These methine and polymethine dyes as well as indamine and indophenol dyes all possess in their chemical structure the following unit.

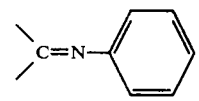

wherein the phenyl group represents an unsubstituted phenyl or substituted phenyl group, for example, a phenyl group substituted with an alkyl group, an alkoxy group, a halogen atom, an amino group, etc.

Dye forming couplers employed in the present invention include those capable of providing yellow, cyan and magenta dyes. Such couplers may be of the so called 4-equivalent or 2-equivalent couplers as described in, for example, U.S. Pat. Nos. 3,277,155 and 3,458,315.

Generally, yellow dye forming couplers have at least one methylene group activated by a carbonyl group (e.g., an openchain ketomethylene group), including β-diketone, β-ketoacylamide such as benzoylacetanilide and α-pivalylacetanilide. Examples of suitable couplers are described in, for example, U.S. Pat. Nos. 2,428,054, 4,026,706, 2,499,966, 2,453,661, 2,778,658, 2,908,573, 3,227,550, 3,253,924, 3,277,155 and 3,384,657, and British Pat. No. 503,752.

Magenta dye forming couplers exemplified by 5-pyrazolone type couplers can also be used in the present invention. This type of couplers are described in, for example, U.S. Pat. Nos. 2,600,788, 2,725,292, 2,908,573, 3,006,759, 3,062,653, 3,152,896, 3,227,550, 3,252,924, 4,026,706, and 3,311,476.

As for other types of magenta dye forming couplers indazolone derivatives are described in Vittum & Weissgerger, *Journal of Photographic Science*, vol. 6, page 158 et seq. (1958); there are further pyrazolinobenzimidazoles as described in, e.g., U.S. Pat. No. 3,061,432, pyrazolo-s-triazoles as described in Belgian Pat. No. 724,427, and 2-cyanoacetylcoumarones as described in, e.g., U.S. Pat. No. 2,115,394, and the like.

Cyan dye forming couplers which can be employed in the present invention include phenol and alpha-naphthol derivatives. This type of compounds are exemplified in U.S. Pat. Nos. 2,275,292, 2,423,730, 2,474,293, 2,895,826, 2,908,573, 3,043,892, 4,026,706, 3,227,550 and 3,253,294.

General descriptions about these coupler compounds are further given in, for example, Kirk-Othmer, *Encyclopedia of Chemical Technology*, vol. 5, pages 822–825 and Glafkides, *Photographic Chemistry*, vol. 2, pages 596–614.

As is described hereinbefore, in the case where such couplers are employed in practicing the present invention, the oxidized aromatic primary amine silver halide developing agent reacts with these couplers to form dyes.

The above-mentioned developing agent includes aminophenol as well as phenylenediamine, each of which can be used individually or in combination thereof.

Representative examples of developing agents which can be combined with a various type of couplers to form organic substrate materials in accordance with the present invention include the following:

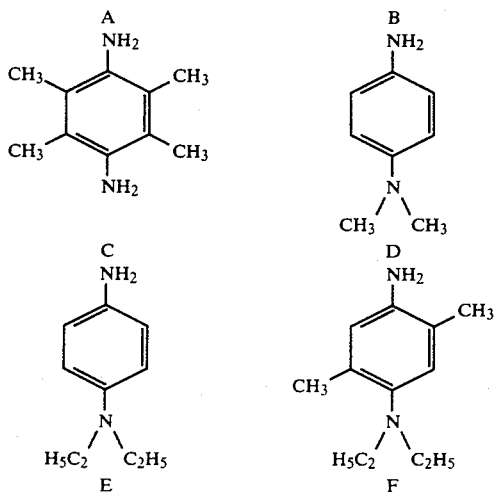

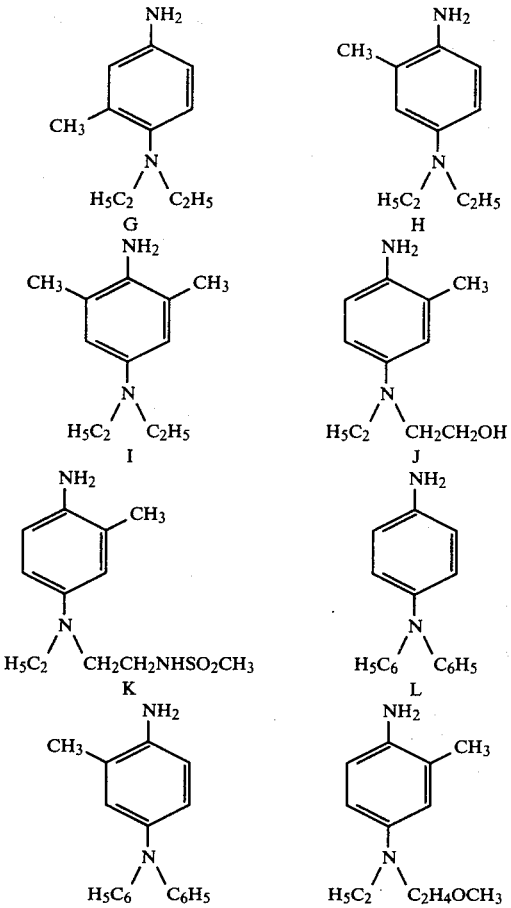

The developing agents illustrated above and others can provide organic substrates upon the reaction with photographic color couplers. Cyan, Magenta and Yellow Couplers which are preferably employed are represented by the formulae (IIa), (IIb) or (IIc) below respectively:

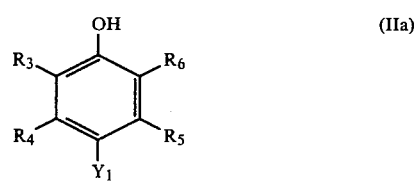

(IIa)

wherein $R_3$, $R_4$, $R_5$ and $R_6$ each represents a hydrogen atom, a halogen atom (e.g., fluorine, chlorine, bromine or iodine), an alkyl group having 1 to 20 carbon atoms (hereafter, all of the alkyl groups referred to with respect of formulae IIa, IIb and IIc may possess 1 to 20 carbon atoms) (e.g., methyl ethyl, octyl, dodecyl, tetradecyl, octadecyl, etc.); an alkyl- or aryl-substituted carbamoyl wherein the aryl moiety has 6 to 10 carbon atoms, (hereafter all of the aryl groups referred to with respect to formulae IIa, IIb and IIc may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R_3$ and $R_4$ may combine with each other to form a six-membered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R_3$, $R_4$, $R_5$ and $R_6$, or the 6-membered ring formed by combining $R_3$ and $R_4$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di(t)-amylphenoxy, etc.); a halogen atom (e.g., chlorine, bromine, fluorine, etc.); and the like.

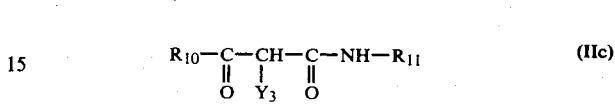

(IIb)

wherein $R_7$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R_8$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc. and $R_9$ represents an aryl group (e.g., phenyl, naphthyl, etc.) said alkyl and aryl groups having the number of carbon atoms discussed above with respect to formula IIa.

D represents an amino group, a carbonylamino group, or a ureido group.

$Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R_7$, the alkyl, amido, N-alkylcarbamoyl, N-alkylsulfamoyl, alkoxycarbonyl or acyloxy group represented by $R_8$, or the aryl group represented by $R_9$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

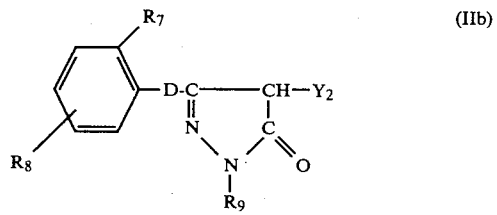

(IIc)

wherein $R_{10}$ represents an alkyl group (e.g., methyl, ethyl, (t)-butyl, (t)-octyl, etc.) or an aryl group (e.g., phenyl) and $R_{11}$ represents an aryl group (e.g., phenyl).

$Y_3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R_{10}$ and the aryl group represented by $R_{11}$ can also be substituted with other substituents, for example, an alkyl group, an aryl group, an alkoxy group, an aryloxy group, an amido group, an N-alkyl-carbamoyl group, an N-alkyl-sulfamoyl group, an acyloxy group, a carboxy group, a sulfo group, a sulfonamido group, a halogen atom, etc.

The above illustrated and other developing agents provide organic substrate materials upon the reaction with couplers including the following:

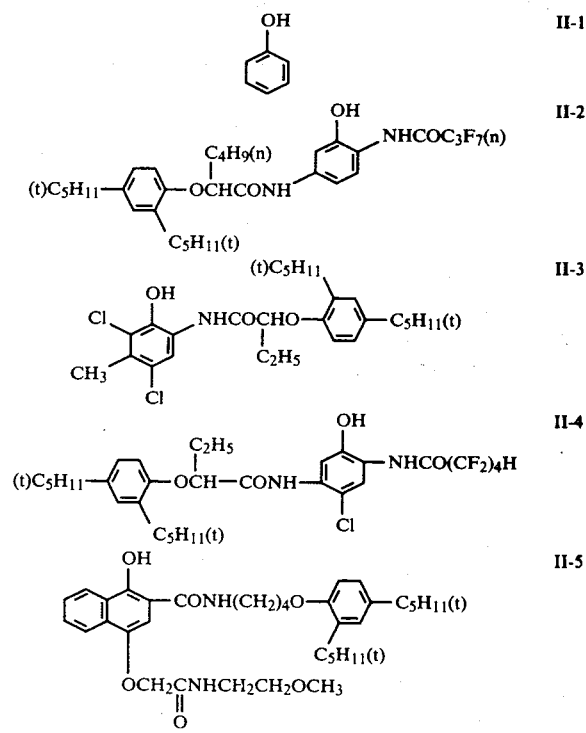

-continued
II-6 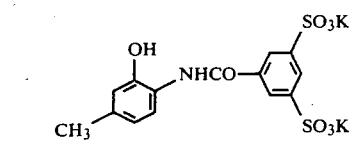
II-7 
II-8 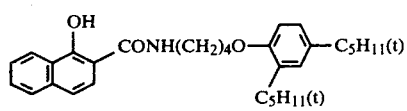
II-9 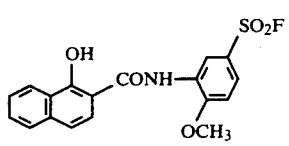
II-10 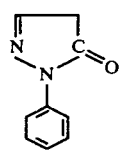
II-11 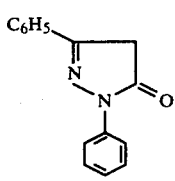
II-12 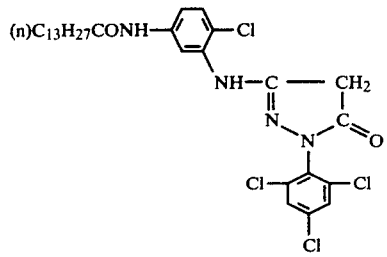
II-13 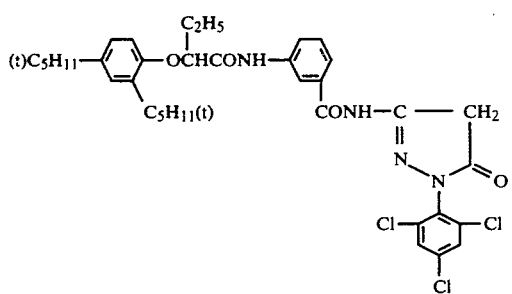
II-14 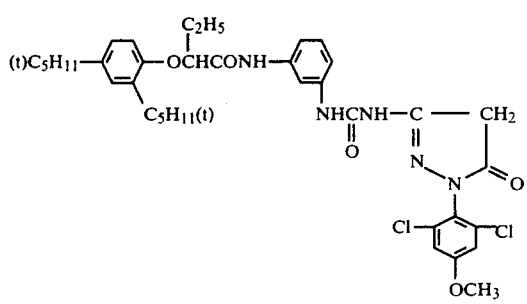
-continued
II-15 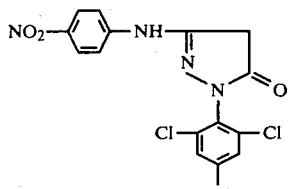
II-16 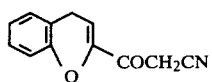
II-17 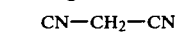
II-18 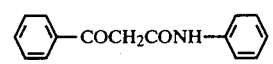
II-19 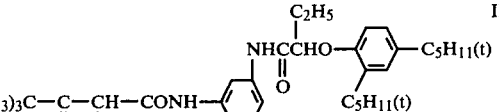
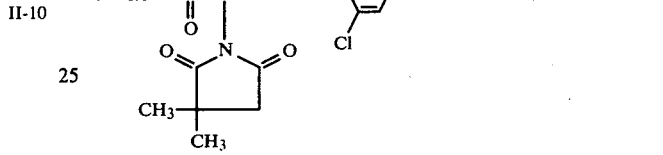
II-20 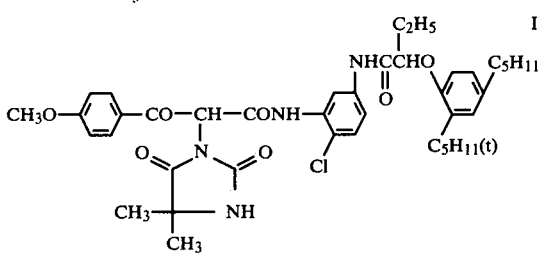
Specific examples of other dyes which can be employed as organic substrate materials upon practice of the present invention include the following:
II-21 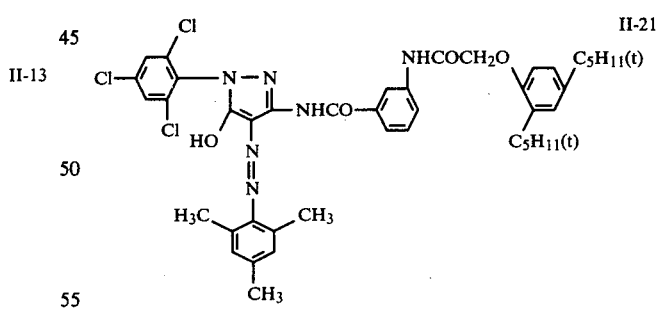
II-22 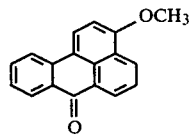
II-23 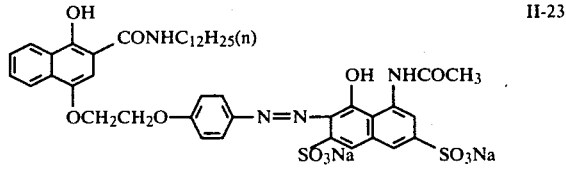

-continued
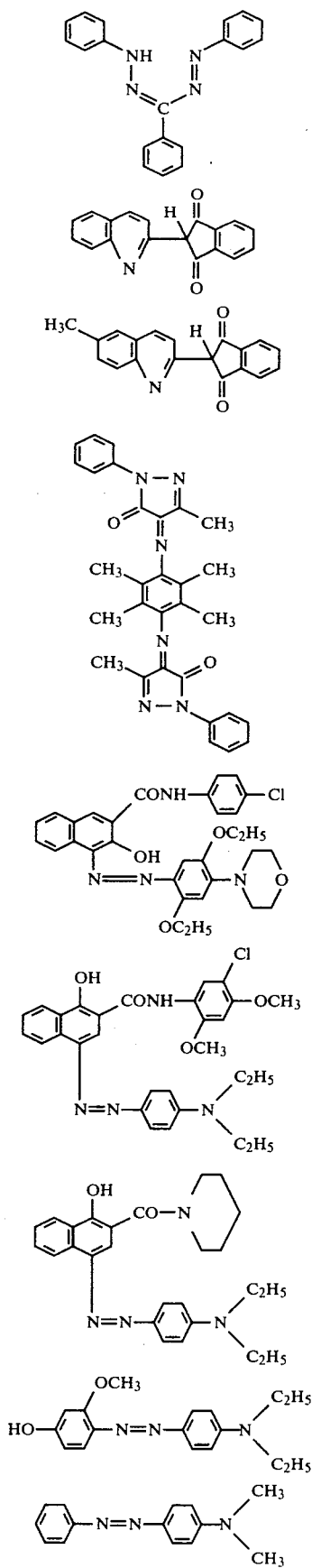
II-24
II-25
II-26
II-27
II-28
II-29
II-30
II-31
II-32
-continued
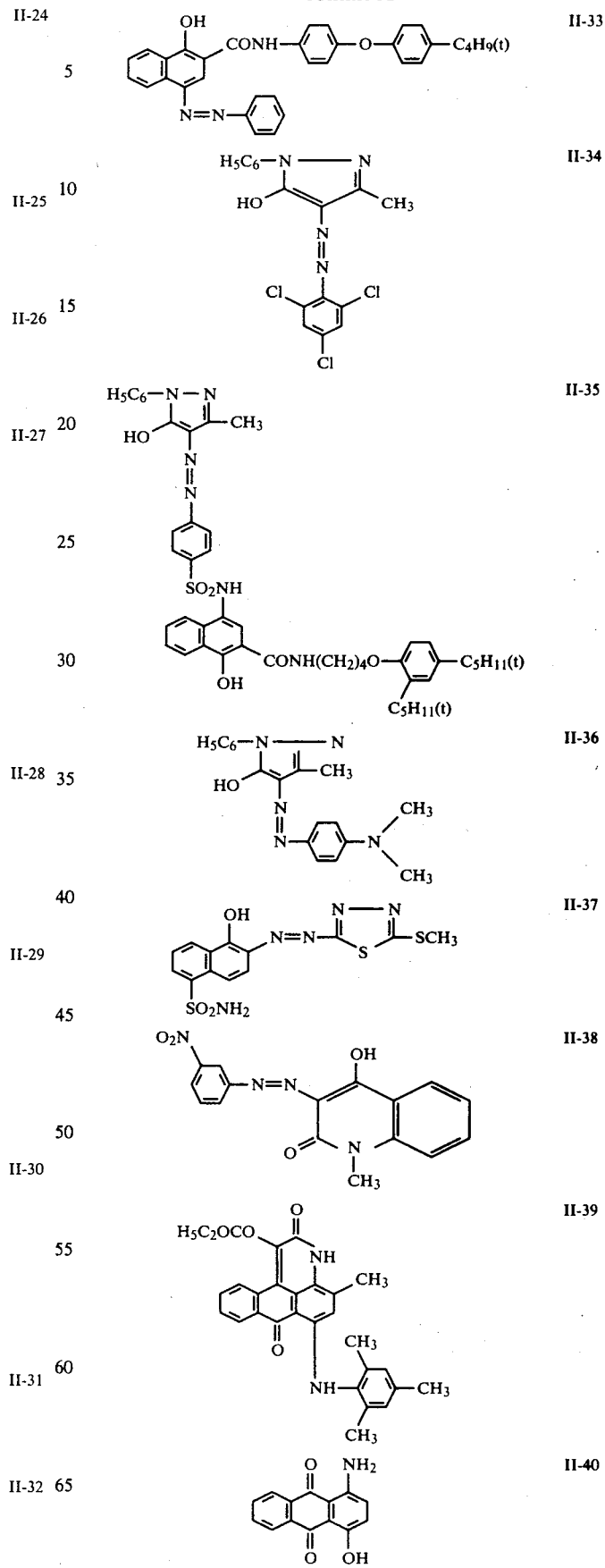
II-33
II-34
II-35
II-36
II-37
II-38
II-39
II-40

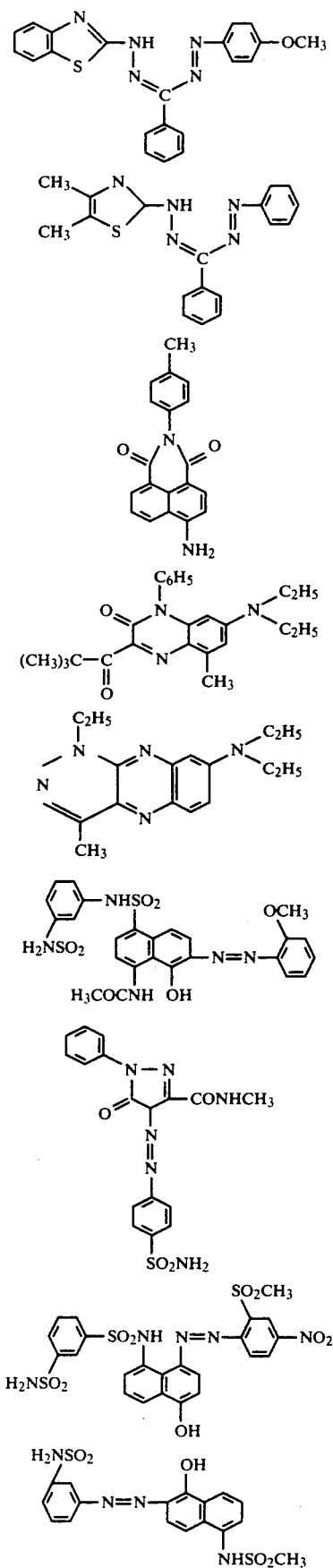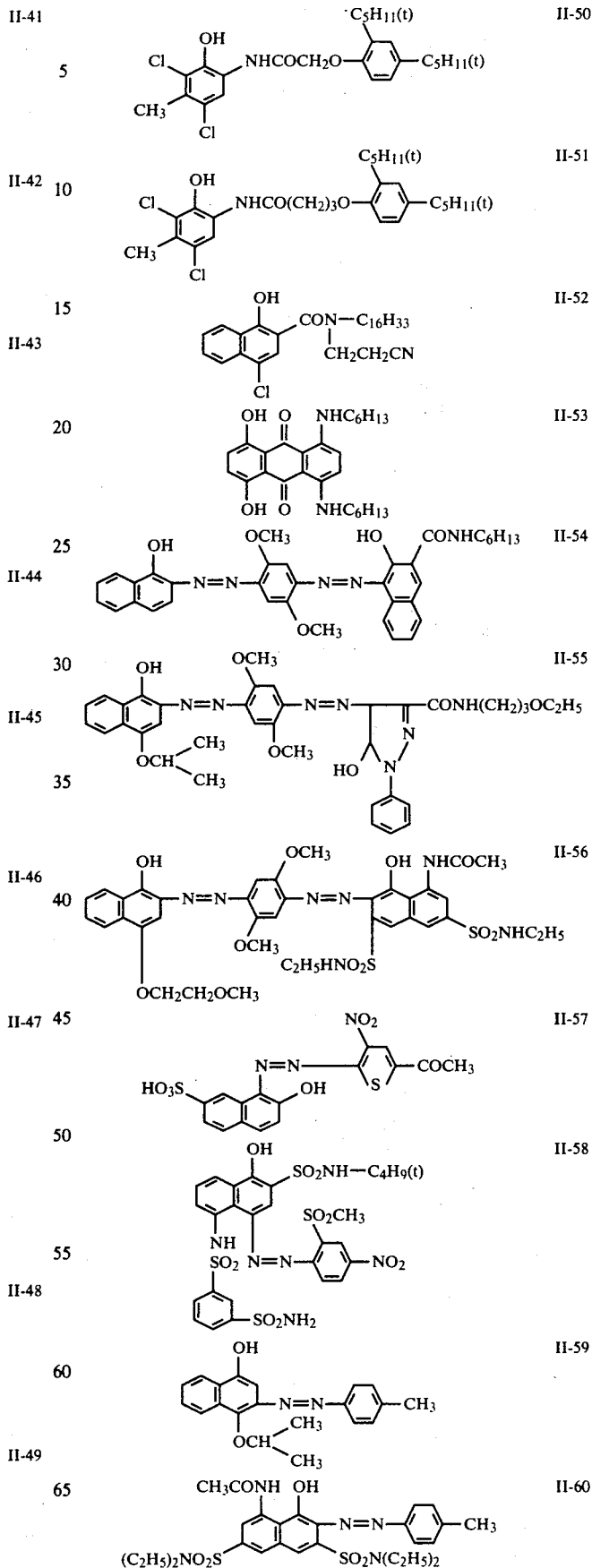

-continued

II-61 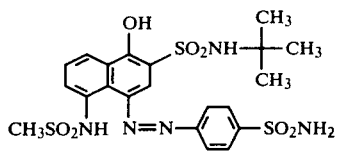

II-62 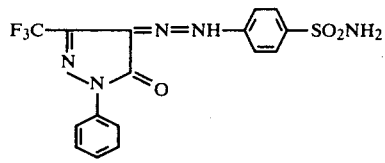

II-63 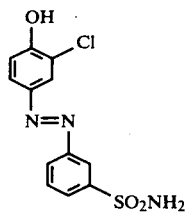

II-64 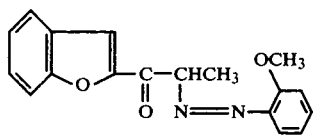

II-65 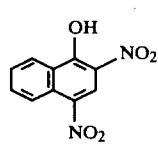

II-66 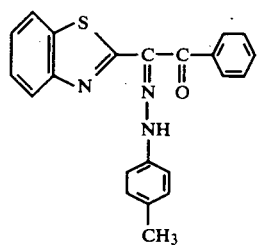

II-67 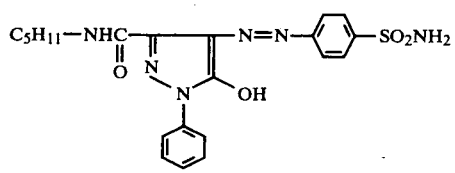

II-68 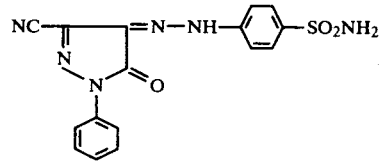

II-69 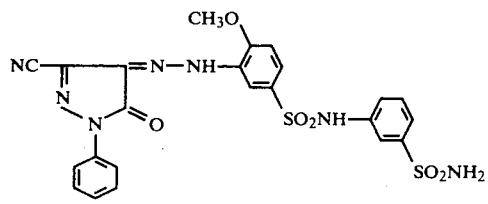

-continued

II-70 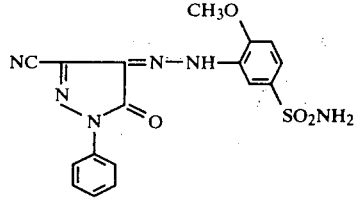

Still other types of dyes which can be preferably used in the present invention include those which are formed by the oxidation of DRR compounds as described in U.S. Published Application B. 351,673, U.S. Pat. Nos. 3,932,381, 3,928,312, 3,931,144, 3,954,476, 3,929,760, 3,942,987, 3,932,380, 4,013,635 and 4,013,633, Japanese patent application (OPI) Nos. 113624/1976, 109928/1976, 104343/1976 and 4819/1977, Japanese patent application 64533/1977 (published as Japanese patent application (OPI) No. 149,328/1978), Research Disclosure, pages 687-74 (1976, November), ibid., No. 13024(1975).

Further the present invention is applicable to those dyes that are released or formed as a result of reaction between DDR couplers and the oxidation product of a color developing agent; such DDR couplers are disclosed in, for example, British Pat. Nos. 840,731, 904,364, 932,272, 1,014,725, 1,038,331, 1,066,352 and 1,097,064, Japanese patent application (OPI) 133021/1976, U.S. Defensive Publication No. T 900,029, U.S. Pat. No. 3,227,550.

Other type of dyes which are preferably employed in the present invention include dye developers as described in Japanese patent publication Nos. 182/1960, 18332/1960, 32130/1973, 43950/1971 and 2618/1974, etc.

Other type of dyes which are employed in the present invention include a variety of dyes employed in silver dye bleach process. Examples of yellow dyes which are usable for this purpose include azo dyes such as Direct Fast Yellow GC (C.I. 29000), Crysophenine (C.I. 24895), etc., benzoquinone dyes such as Indigo Golden Yellow IGK(C.I. 59101), Indigosol Yellow 2GB(C.I. 61726), Mikethrene Yellow GC(C.I. 67300), Indanthrene Yellow 4GK(C.I. 68405), Argosol Yellow GCA-CF(C.I. 67301), Indanthrene Yellow GF(C.I. 68420), etc., anthraquinone dyes, soluble vat dyes with fused ring structure, other types of vat dyes, etc. Specific examples of magenta dyes include Sumilight Supra Rubinol B(C.I. 29225), Benzobrilliant Gelanine B(C.I. 15080), etc., indigoid dyes such as Indigosol Brilliant Pink IR(C.I. 73361), Indigosol Violet 15R(C.I. 67895), Indigosol Red Violet IRRL(C.I. 59316), Indanthrene Red Violet RRK(C.I. 67895), Mikethrene Brilliant Violet BBK(C.I. 6335), etc., soluble vat dyes comprising anthraquinone hetero polycyclic compounds, and still other types of vat dyes. Specific examples of cyan dyes include azo dyes such as Direct Sky Blue 6B(C.I. 24410), Direct Brilliant Blue 2B(C.I. 22610), Sumilight Supra Blue G(C.I. 34200), etc., phthalocyanine dyes such as Sumilight Supra Turkeys Blue G(C.I. 74180), Mikethrene Brilliant Blue 4G(C.I. 74140), etc., Indanthrene Turkeys Blue 5G(C.I. 69845), Indanthrene Blue GCD(C.I. 73066), Indigosol 04G(C.I. 73046), Anthrasol Green IB(C.I. 59826), etc.

While the mechanism whereby the complex of the present invention improves light fastness is not entirely clear, it is believed that upon exposure to light the organic subsrtate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As stated hereinbefore, the metal chelate complex in accordance with the present invention acts to stabilize organic substrate materials to light, and can be incorporated in at least one of emulsion layers composing a color photographic film or in the whole layers thereof. The metal chelate compound can also be present in any layer involved in the light insensitive portion of a color transfer material.

These complexes can be provided for stabilizing organic substrate materials to light by incorporating them into a hydrophilic colloid composing photographic layers, as a solution, after dissolving these complexes in solvents that do not adversely affect photographic properties, which are chosen from organic solvents having low melting point or organic solvents compatible with water, for example, alcohols (e.g., methanol, ethanol, isopropanol, butanol, etc.), ethers (dimethyl ether, ethyl methyl ether, diethyl ether, 1-ethoxypropane, etc.), glycols (1,2-ethanediol, 1,2-propanediol, 1,3-propanediol, etc.), ketones (acetone, ethyl methyl ketone, 3-pentanone, etc.), esters (ethyl formate, methyl acetate, ethyl acetate, etc.), amides (formamide, acetamide, succinamide, etc.). It is desired that this incorporation be performed prior to coating, such as when the silver halide photographic emulsion is prepared, when the couplers are emulsion-dispersed, when a photographic coating solution is prepared, etc.

In order to introduce these chelate compounds into hydrophilic colloid composing photographic layers, methods similar to those as described with respect to dispersion of couplers are applicable. That is, U.S. Pat. Nos. 2,304,939 and 2,322,027 disclose the use of high boiling point organic solvents for dissolving these materials. Other methods applicable to the present purpose include those as described in U.S. Pat. Nos. 2,801,170, 2,801,171 and 2,949,360 wherein low boiling point or water soluble organic solvents are employed in conjunction with high boiling point solvents.

High boiling point solvents effectively employed for the dispersion of the organic substrate material as well as the metal chelate involved in the present invention include di-n-butyl phthalate, benzyl phthalate, triphenyl phosphate, tri-o-cresyl phosphate, diphenyl mono-p-tert-butylphenyl phosphate, monophenyl-di-p-tert-butylphenyl phosphate, diphenylmono-o-chlorophenyl phosphate, monophenyl-di-o-chlorophenyl phosphate, 2,4-di-n-amylphenol, 2,4-di-tert-amylphenol, N,N-diethyllauryl amide; trioctyl phosphate and trihexyl phosphate and described in U.S. Pat. No. 3,676,137, etc.

Low boiling point and water soluble organic solvents which can be advantageously employed in combination with these high boiling point solvents are disclosed in, for example, U.S. Pat. Nos. 2,801,171, 2,801,170 and 2,949,360.

These solvents include:

(1) solvents which are substantially immiscible with water such as methyl acetate, ethyl acetate, propyl acetate, butyl acetate, isopropyl acetate, ethyl propionate, sec-butyl alcohol, ethyl formate, butyl formate, nitromethane, carbon tetrachloride, chloroform, etc., and (2) water miscible organic solvents such as, for example, methyl isobutyl ketone, β-ethoxyethyl acetate, β-butoxytetrahydrofurfuryl adipate, diethylene glycol monoacetate, methoxytriglycol acetate, acetonylacetone, diacetone alcohol, ethylene glycol, diethylene glycol, dipropylene glycol, acetone, methanol, ethanol, acetonitrile, dimethyl formamide, dioxane, etc.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc. together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein as a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

In the case of a photographic material the substrate material (the dye image) and the complex each may be present in one or more of the hydrophilic colloid layers making up the photographic element (film, paper, diffusion transfer unit, etc.). It is preferred that the metal chelate complex and the organic substrate material be present (i.e., co-exist) in the same emulsion layer, of course, the effects of the present invention can also be accomplished when the complex and substrate are present in contiguous layers as long as diffusion is allowed to occur between the layers. Were any (further) undesirable diffusion to occur, conventional mordanting techniques could be applied to the present invention. In the case of incorporating the complex into a silver halide emulsion layer, the complex can be incorporated into each emulsion layers making up the photographic element in this case the total amount of complex is present in the amounts set forth above. The complex and substrate may be present in non-light sensitive elements or layers as well, such as the dye image receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse further into any other layer(s) so that the complex is easily maintained in the vicinity of the dye. In the case where the substrate material and the complex are contained in such a light insensitive image recording layer, these materials should preferably be mordanted. In such a case, the chelate complex needs to posses a ligand suited for retaining it in the mordanted layer of the image receiver so that the complex does not diffuse and leave the vicinity of the dye substrate to be stabilized therewith.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,006, 3,253,915, 3,227,550, 3,227,551, 3,227,552, 3,415,646, 3,594,164 and 3,594,165 and Belgian Pat. Nos. 757,959 and 757,960.

The complex compound and the substrate material embodying the present invention can be employed together with materials as described in *Product Licensing Index*, vol. 92, No. 9232 (1971, December), pp 107–110 according to the methods also as described therein. Reference is made to Chapters I, II, III, IV, V, VII, VIII, IX, X, XI, XII, XIII, XIV, XV, XVI, XVII, XVIII and XXIII.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably, in an amount of 0.1 to 1000 mol%, and most preferably, in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^4$ micromoles per square meter of the photographic material. A more preferably range is from about 100 to about $3 \times 10^3$ micromoles per square meter of the photographic product.

The substrate material which is employed for practicing the present invention usually has the absorption maximum at an wavelength shorter than about 800 nm. This absorption maximum is preferably in a range of from about 300 to about 800 nm, and more preferably from about 400 to 800 nm.

Any type of support material ordinarily employed in photographic light sensitive materials can be used in the present invention, including, for example, cellulose nitrate film, a cellulose acetate film, a cellulose acetate-butyrate film, a cellulose acetate propionate film, a polystyrene film, a polyethylene terephthalate film, a polycarbonate film, a laminate sheet product comprising the aforesaid films, paper, etc. Particularly preferred ones are baryta coated paper, paper laminated or coated with an α-olefin polymer such as polyethylene, polypropylene or the like comprising $C_2$-$C_{10}$ α-olefins, those plastic films that are disclosed in Japanese Patent Publication No. 19068/1972 which are provided with a roughned surface of an improved adhesive property to different polymeric materials, etc.

To prepare a photographic light sensitive material for the present invention, various hydrophilic colloids are employed. Hydrophilic colloid materials used as a binder for photographic emulsion coating and/or other photographic coatings include, for example, gelatin, colloidal albumin, casein, cellulose derivatives such as carboxymethyl cellulose, hydroxyethyl cellulose, etc., carbohydrate derivatives such as agar-agar, sodium alginate, starch and its derivatives, etc., synthetic hydrophilic polymers such as polyvinyl alcohol, poly-N-vinylpyrrolidone, acrylic copolymers, maleic anhydride copolymers, polyacrylamide, derivatives from these synthetic polymers including partially hydrolized products thereof, etc. If necessary, two or more of these colloidal materials are employed simultaneously provided that they are mutually compatible.

Of these colloid materials, the most extensively used is gelatin, which can be replaced wholly or partially with synthetic polymeric materials or with so called gelatin derivatives. Such gelatin derivatives can be prepared by modifying or treating gelatin with reagents which possess a functional group capable of reacting with the reactive groups contained in the gelatin molecule such as amino, imino, hydroxy or carboxy group, or by grafting to the gelatin molecular chain a suitable synthetic polymer chain.

The photographic emulsion coating or other photographic coatings composing the photographic material employed in the present invention can involve synthetic polymer materials such as, for example, a latex of vinyl polymer dispersed in water and those which can improve the dimensional stability of the light sensitive material, singly or in combination. The photographic light sensitive material can contain one or more of such materials and in some cases, in conjunction with a hydrophilic water permeable colloid.

Silver halide photographic emulsions used in the present invention are usually prepared by mixing an aqueous solution of a water soluble silver salt (e.g., silver nitrate) with an aqueous solution of a water soluble halide salt (e.g., potassium bromide) in the presence of a water soluble polymeric material such as gelatin. The resulting silver halide includes not only silver chloride and silver bromide, but also those containing halogen mixtures such as chlorobromide, iodobromide, chloroiodobromide, etc. Any methods well known in the art can be adopted to prepare grains of such a silver halide, self evidently including single and double jet methods, control double jet method, etc. One can also blend two or more kinds of silver halide photographic emulsion each of which has been prepared independently.

A number of additives can be incorporated into the photographic emulsion in order to prevent deterioration of photographic speed or generation of fog during the manufacturing procedures, storage period and photographic processing. Such additives include various heterocyclic compounds such as 4-hydroxy-6-methyl-1,3,3a,7-tetrazaindene, 3-methylbenzothiazole, 1-phenyl-5-mercaptotetrazole, etc., Hg containing compounds, mercapto compounds, metal salts, etc.

The photographic emulsion used in the present invention can be chemically sensitized according to one of known methods. Chemical sensitizers include gold compounds such as chloroaurates, gold trichloride, etc., salts of noble metals such as Pt, Pd, Ir, Rd, etc., those sulfur compounds that can react with silver salts to yield silver sulfide (e.g., sodium thiosulfate), and other reducing substances such as stannous salts, amines, etc.

The photographic emulsion employed in the present invention can be spectrally sensitized or super sensitized using cyanine dyes such as cyanine, merocyanine, carbocyanine individually or assortedly among themselves or with styryl type dyes. The choice of dyes depends on the spectral region to be sensitized, the degree of spectral sensitivity, etc., which vary depending upon the expected application of the resulting product.

The hydrophilic colloid contained in the photographic material employed in the present invention can be, if desired, cross linked with a variety of hardening agents such as aldehydes, active halogen compounds, vinyl sulfones, carbodiimides, N-methylol compounds, epoxy compounds, etc.

According to one embodiment of the present invention where the method of the invention is applied to a color photographic material, the color photographic material is, after imagewise exposed, processed in an ordinary manner to provide color images. Such processing comprises color development, bleach and fix, to which other steps such as rinse with water or stabilization may be introduced if necessary. Some of these processing operations can be united into a mono-bath step; a typical example is a so-called "blix" operation comprising bleach and fix. The color development is carried out in an alkaline solution containing an aromatic primary amine developing agent. Preferred compounds as the developing agent include Compounds (A) to (L) already illustrated in the specification.

As another embodiment, the method of the present invention is applied to a color photographic material of diffusion transfer type. In this case, processing is effected within the photographic material automatically. Suitable developing agents which are contained in a rupturable container include, in addition to Compounds (A) to (L), N-methylaminophenol, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylenediamine, etc.

For the formation of color images in the photographic materials used in the present invention, a variety of methods can be employed which are based on the following principles; The coupling reaction between a dye forming color coupler and the oxidation product of a p-phenylenediamine type chromogenic developing agent, processing using a dye developer, an oxidative cleavage reaction of a DRR compound, the dye releasing reaction caused by the coupling of a DDR coupler, a dye forming reaction caused by the coupling of a DDR coupler, silver dye bleach process and other conventionally known processes.

Therefore, where the method of the present invention is applied to photographic light sensitive materials, the present invention is applicable to a wide variety of color photographic light sensitive materials such as a color positive film, a color printing paper, a color negative film, a color reversal film, film units for color diffusion transfer, silver dye bleach photographic materials, etc.

EXAMPLE 1

In 3 ml of tricresyl phosphate and 5 ml of ethyl acetate, was dissolved 0.1 g of 1-(2,4,6-trichlorophenyl)-3-(2-chloro-5-tetradecanamido)anilino-4-[4-(N-ethyl-N-β-methanesulfonamidoethyl)aminophenylimino]-5-oxo-2-pyrazoline. The resulting solution was emulsion-dispersed in 10 g of 10% gelatin containing 1 ml of a 1% sodium dodecylbenzenesulfonate aqueous solution. Thereafter, the emulsion dispersion was mixed with 10 g of 10% gelatin and the mixture was coated onto a paper support, both surfaces of which being laminated with polyethylene, and then dried, which was designated Sample A.

In a similar manner, Sample B in which 20 mg of Compound I-1 of the present invention was added at the time when the above described emulsion dispersion was prepared followed by coating in a manner similar to Sample A, and Samples C and D in which 25 mg and 250 mg of 2,5-di-tert-octylhydroquinone known as a light fading preventing agents for a dye was added respectively followed by coating in a manner similar to Sample A, were prepared, respectively. The coated amount of the dye was 60 mg/m$^2$ in all cases. The coated amount of the fade preventing agent was 12 mg/m$^2$ in Sample B, 15 mg/m$^2$ in Sample C and 150 mg/m$^2$ in Sample D.

In a Cannon Tester (light intensity, 200,000 luxes), a 48 hour fading test was performed on pieces of these samples superimposed with a UV cut filter C-40, manufactured by Fuji Photo Film Co., Ltd. The measurement was performed using a Macbeth Densitometer RD 514 Model loaded with a green filter of status AA grade. The results are shown in Table 1.

TABLE 1

| Sample | Initial density | Density after 48 hrs. |
|--------|-----------------|-----------------------|
| A | 0.82 | 0.04 |
| B | 0.80 | 0.72 |
| C | 0.80 | 0.12 |
| D | 0.81 | 0.39 |

It was confirmed that Sample B containing Compound I-1 of the present invention showed extremely less color fading as compared to other Samples A, C and D, and particularly with Samples C and D, these samples were hardly effective in preventing color fade notwithstanding that 2,5-di-tert-octylhydroquinone was incorporated in amounts equimolar to or 10 times moles that of Compound I-1 of the present invention, respectively. These results indicate that Compound I-1 of the present invention possesses a surprising effect in preventing color fade of the dye.

EXAMPLE 2

Into a solvent mixture comprising 0.2 cc of 1N-NaOH and 2 cc of methanol was dissolved 0.1 g of Compound II-23. The resulting solution was added to 10 g of 10% gelatin.

The mixture was coated onto a paper support, both surfaces of which being laminated with polyethylene, so that coated amount of Compound II-23 was 80 mg/m$^2$ on a dry basis (Sample E).

In a similar manner Sample F was prepared except that a solution of 60 mg of Compound I-3 of the present invention in 2 cc of methanol was added immediately before coating followed by coating in the same manner as in Sample E. Further, Sample G was prepared in a similar manner for comparison except that 100 mg of α-tocophenol acetate, a known color fade preventing agent of a dye, was added followed by coating in the same manner. The coated amount of fade preventing agent was 48 mg/m² in Sample E and 80 mg/m² in Sample F.

These samples were subjected to a 12 hour fade test, superimposed with a UV cut filter, in a manner similar to Example 1. The measurement was performed in a manner similar to Example 1, using the Macbeth Densitometer. The results are shown in Table II.

TABLE II

| Sample | Initial density | Density after 12 hrs. |
|---|---|---|
| E | 0.91 | 0.08 |
| F | 0.93 | 0.74 |
| G | 0.91 | 0.19 |

From the results shown in the table, it is seen that the light fastness effect achieved by Compound I-3 of the present invention is markedly improved.

EXAMPLE 3

In a solvent mixture of 30 ml of tricresyl phosphate, 5 ml of dimethylformamide and 15 ml of ethyl acetate was dissolved 10 g of magenta coupler, 1-(2,4,6-trichlorophenyl)-3-[(2-chloro-5-tetradecanamido)anilino)]-2-pyrazoline-5-one. The solution was emulsion dispersed into 80 g of a 10% aqueous gelatin solution containing 8 ml of a 1% aqueous sodium dodecylbenzene sulfonate solution.

Then, the emulsified dispersion was mixed with 145 g (containing 7 g as Ag) of green sensitive silver chlorobromide (Br content, 50 mol%) and sodium dodecylbenzenesulfonate was further added thereto as a coating aid. The coating solution was coated onto a paper support, both surfaces of which being laminated with polyethylene (Sample H). The coated amount of the coupler was 400 mg/m².

Sample I was prepared in a similar manner except that 4.5 g of Compound I-3 of the present invention was added at the time when the aforesaid emulsified dispersion was prepared followed by coating in a manner similar to Sample H. Further, Sample J was prepared in a similar manner except that 1.9 g of known 2,2'-methylenebis(4-methyl-6-tert-butylphenol) was added as a color fade preventing agent of the dye followed by coating in a similar manner to Sample H. The coated amounts of Compound I-3 and the butylphenol were 180 mg/m² and 76 mg/m², respectively.

These samples were exposed for 1 sec. at 1,000 luxes, followed by processing with the following processing solutions.

| Developer: | |
|---|---|
| Benzyl alcohol | 15 ml |
| Diethylene triamine pentaacetate | 5 g |
| KBr | 0.4 g |
| Na₂SO₃ | 5 g |
| Na₂CO₃ | 30 g |
| Hydroxylamine sulfate | 2 g |
| 4-Amino-3-methyl-N-ethyl-N-β-(methanesulfonamido)ethylaniline. 3/2 H₂SO₄ . H₂O | 4.5 g |
| Water to make | 1 l |
|  | pH 10.1 |
| Bleach-fixing solution: | |
| Ammonium thiosulfate (70 wt%) | 150 ml |
| Na₂SO₃ | 5 g |
| Na[Fe(EDTA)] | 40 g |
| EDTA | 4 g |
| Water to make | 1 l |

| Processing step: | Temperature | Time |
|---|---|---|
| Developer | 33° C. | 3 mins. 30 secs. |
| Bleach-fixing solution | 33° C. | 1 min. 30 secs. |
| Water-rinsing | 28°–35° C. | 3 mins. |

Each of the samples thus formed dye images was subjected to a 4 week color fade test using a fluorescent light color fademeter (20,000 luxes), superimposed with a UV cut filter C-40 which cut wavelengths smaller than 400 nm, manufactured by Fuji Photo Film Co., Ltd. The results are shown in Table III. The measurement was performed using a Macbeth Densitometer RD-514 Model (status AA filter) and the density change at an area of initial density 2.0 was measured.

TABLE III

| Sample | Density at a 2.0 initial density portion after color fade test | Dye remaining rate* (%) |
|---|---|---|
| H | 0.82 | 41 |
| I | 1.82 | 91 |
| J | 1.46 | 73 |

*Dye remaining rate = $\left(\dfrac{\text{density after color fading}}{2.0}\right) \times 100$ From the results shown in the table above, it is seen that Compound I-3 of the present invention is an effective color fade preventing agent.

EXAMPLE 4

A solution of 15 mg of a dye having the structure below and 500 mg of polycarbonate, Lexan 145 (tradename, manufactured by General Electric Co., Ltd.) in 100 ml of dichloromethane was coated onto a glass plate using a spinner. A magenta-colored film of 5.5μ thickness was thus prepared as Sample K.

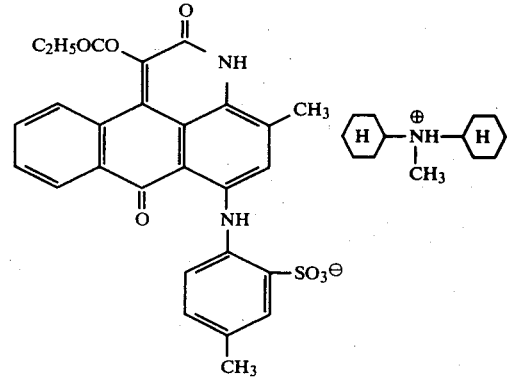

In a similar manner, three(3) colored films were prepared as Samples L, M and N except that Compounds I-1, I-16 and I-17 were further incorporated into the solution, respectively.

The coating rate of the dye and the fade prevention compounds were 500 mg/m² and 50 mg/m², respectively.

The thus obtained films were exposed to sunlight for one month and a color fading test was carried out. The results obtained are shown in Table IV below, in which density was measured at 550 nm.

TABLE IV

| Sample | Initial density | Density after fading |
|---|---|---|
| K | 1.0 | 0.50 |
| L | 1.0 | 0.80 |
| M | 1.0 | 0.78 |

TABLE IV-continued

| Sample | Initial density | Density after fading |
| --- | --- | --- |
| N | 1.0 | 0.70 |

It can be clearly understood from the results above that the samples containing the compounds of the present invention provide excellent fade preventing effect in particular, the effect provided by the compound containing Ni as a chelate metal is markedly significant.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oil droplets and as a result, photographically undesired interaction with silver halide (e.g., desensitization) is avoidable.

(4) Due to its extremely high solubility, a small amount of the complex is sufficient to effect light fastness; conversely, a large amount can also be employed as in the case of umbrellas, agricultural vinyl cover sheets, etc.

(5) Where the chelate is used in a photographic element, no adverse effect on photographic properties is encountered.

(6) The complex is the first fading prevention agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What is claimed is:

1. A diffusion transfer color photographic material comprising a photosensitive element and an image receiving element said image receiving element comprising a support having thereon a mordanting layer containing a complex of the formula I

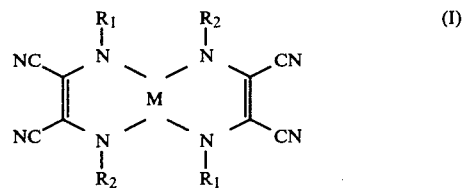

wherein M represents Ni, Pd or Pt; $R_1$ and $R_2$, which may be the same or different, each represents a hydrogen atom, an alkyl group, an aryl group, an acyl group, an alkoxycarbonyl group, an aryloxycarbonyl group, an alkylsulfonyl group, an arylsulfonyl group or a carbamoyl group.

2. The diffusion transfer color photographic material of claim 1 wherein in said formula (I), M is Ni.

* * * * *